United States Patent
Henry et al.

(10) Patent No.: US 12,072,333 B2
(45) Date of Patent: Aug. 27, 2024

(54) METHOD AND APPARATUS FOR SELECTIVE REMOVAL OF CELLS FROM A CELL SUSPENSION BY MECHANICAL LYSIS

(71) Applicants: UNIVERSITY OF IOWA RESEARCH FOUNDATION, Iowa City, IA (US); SYNDERBIO, INC., Coralville, IA (US)

(72) Inventors: Michael D. Henry, Iowa City, IA (US); Benjamin Krog, Iowa City, IA (US); Sarah Vigmostad, Iowa City, IA (US); Mike Cable, Iowa City, IA (US)

(73) Assignees: University of Iowa Research Foundation, Iowa City, IA (US); SynderBio, Inc., Coralville, IA (US)

( * ) Notice: Subject to any disclaimer, the term of this patent is extended or adjusted under 35 U.S.C. 154(b) by 1488 days.

(21) Appl. No.: 16/346,562

(22) PCT Filed: Nov. 2, 2017

(86) PCT No.: PCT/US2017/059768
§ 371 (c)(1),
(2) Date: May 1, 2019

(87) PCT Pub. No.: WO2018/085572
PCT Pub. Date: May 11, 2018

(65) Prior Publication Data
US 2019/0265239 A1    Aug. 29, 2019

Related U.S. Application Data

(60) Provisional application No. 62/416,609, filed on Nov. 2, 2016.

(51) Int. Cl.
| | |
|---|---|
| G01N 33/569 | (2006.01) |
| C12Q 1/6806 | (2018.01) |
| G01N 1/28 | (2006.01) |
| G01N 1/34 | (2006.01) |
| G01N 33/483 | (2006.01) |

(52) U.S. Cl.
CPC ..... *G01N 33/56966* (2013.01); *C12Q 1/6806* (2013.01); *G01N 1/286* (2013.01); *G01N 33/4833* (2013.01); *G01N 2001/2866* (2013.01); *G01N 1/34* (2013.01)

(58) Field of Classification Search
None
See application file for complete search history.

(56) References Cited

U.S. PATENT DOCUMENTS

| | | | |
|---|---|---|---|
| 6,942,169 B2 | 9/2005 | Sparks | |
| 7,319,021 B2 | 1/2008 | Engel et al. | |
| 7,494,771 B2 | 2/2009 | Picard et al. | |
| 7,723,095 B2 | 5/2010 | Cleuziat et al. | |
| 8,993,306 B2 | 3/2015 | Rudorfer | |
| 9,024,008 B2 | 5/2015 | Kiss et al. | |
| 9,063,118 B2 | 6/2015 | Henry et al. | |
| 9,121,801 B2 * | 9/2015 | Clark | C12M 37/04 |
| 9,365,816 B2 | 6/2016 | Li et al. | |
| 9,441,265 B2 | 9/2016 | Chiesl | |
| 2005/0064598 A1 | 3/2005 | Yuan et al. | |
| 2005/0070944 A1 | 3/2005 | Holl et al. | |
| 2014/0370593 A1 | 12/2014 | Achneck et al. | |
| 2015/0316456 A1 | 11/2015 | Henry et al. | |

FOREIGN PATENT DOCUMENTS

| | | |
|---|---|---|
| WO | 2012129360 A2 | 9/2012 |
| WO | 2016070007 A1 | 5/2016 |

OTHER PUBLICATIONS

De Jong, J. S., P. J. Van Diest, and J. P. A. Baak. "Number of apoptotic cells as a prognostic marker in invasive breast cancer." British Journal of Cancer 82.2 (2000): 368-373. (Year: 2000).*
Chen, X , et al., "Continuous flow microfluidic device for cell separation, cell lysis and DNA purification", Anal Chim Acta 584(2), 237-243 (2007).
Chen, X , et al., "On-line cell lysis and DNA extraction on a microfluidic biochip fabricated by microelectromechanical system technology", Electrophoresis 29(9), 1844-1851 (2008).
Di Carlo, D , et al., "Reagentless mechanical cell lysis by nanoscale barbs in microchannels for sample preparation", Lab Chip 3(4), 387-291 (2003).
Kim, J , et al., "Microfluidic sample preparation: cell lysis and nucleic acid purification", Integr Biol (Camb) 1(10), 574-586 (2009).
Mitchell, M , et al., "Lamin A/C deficiency reduces circulating tumor cell resistance to fluid shear stress", Am J Physiol Cell Physiol 309, C736-C746 (2015).
Morton, K , et al., "Crossing microfluidic streamlines to lyse, label and wash cells", Lab Chip 8(9), 1448-1453 (2008).
Patent Cooperation Treaty , International Searching Authority, Search Report and Written Opinion for PCT/US2017/059768, 9 pages, Jan. 25, 2018.
Salehi-Reyhani, A , et al., "Chemical-free lysis and fractionation of cells by use of surface acoustic waves for sensitive protein assays", Anal Chem 87(4), 2161-2169 (2015).
Siegrist, J , et al., "Validation of a centrifugal microfluidic sample lysis and homogenization platform for nucleic acid extraction with clinical samples", Lab Chip 10(3), 363-371 (2010).

(Continued)

*Primary Examiner* — Robert J Yamasaki
(74) *Attorney, Agent, or Firm* — Viksnins Harris Padys Malen LLP

(57) ABSTRACT

In some embodiments, the present disclosure provides an apparatus and methods for selectively lysing cells from a cell suspension including disassociating a population of cells from a tissue sample, the population of cells including a population of one or more viable cells and a population of one or more dead and dying cells, exposing the population of cells to at least one pulse of fluid shear stress having a force along a conduit wall of from about 500 dyn/cm2 to about 2500 dyn/cm2 to substantially lyse the population of one or more dead or dying cells, leaving the population of one or more viable cells substantially intact, and collecting the population of one or more viable cells.

16 Claims, 10 Drawing Sheets

(56) References Cited

OTHER PUBLICATIONS

Triantafillu, U , et al., "Fluid shear stress induces cancer stem cell-like phenotype in MCF7 breast cancer cell line without inducing epithelial to mesenchymal transition", International Journal of Oncology 50, 993-1001 (2017).
Vennin, C , et al., "Transient tissue priming via ROCK inhibition uncouples pancreatic cancer progression, sensitivity to chemotherapy, and metastasis", Sci Transl Med 9, eaai8504, 19 pages (2017).
Wurm, M , et al., "Mechanical disruption of mammalian cells in a microfluidic system and its numerical analysis based on computational fluid dynamics", Lab Chip 12(6), 1071-1077 (2012).
Yun, S , et al., "Handheld mechanical cell lysis chip with ultra-sharp silicon nano-blade arrays for rapid intracellular protein extraction", Lab Chip 10(11), 1442-1446 (2010).

* cited by examiner

| SAMPLE # | FLOW RATE (μL/sec) | PULSES (#) | Q1: FITC-A-, HOECHST 33258-A+ | Q2: FITC-A+, HOECHST 33258-A+ | Q3: FITC-A+, HOECHST 33258-A- | Q4: FITC-A-, HOECHST 33258-A- | Q1+Q2+Q3 | VIABLE (Q4):DEAD/DYING (Q1,2,3) |
|---|---|---|---|---|---|---|---|---|
| 1 | 0 | 0 | 31.5 | 31.8 | 2.47 | 34.2 | 65.77 | 0.52 |
| 2 | 0 | 0 | 30.5 | 26.5 | 3.73 | 39.3 | 60.73 | 0.65 |
| 3 | 0 | 0 | 8.06 | 16.7 | 5.11 | 70.2 | 29.87 | 2.35 |
| 4 | 20 | 2 | 3.68 | 14.8 | 4.98 | 76.6 | 23.46 | 3.27 |
| 5 | 20 | 2 | 5.76 | 17 | 5.36 | 71.9 | 28.12 | 2.56 |
| 6 | 20 | 10 | 8.51 | 17.2 | 3.98 | 70.3 | 29.69 | 2.37 |
| 7 | 20 | 10 | 10.2 | 19.4 | 4.75 | 65.6 | 34.35 | 1.91 |
| 8 | 50 | 2 | 10.8 | 16.3 | 3.62 | 69.3 | 30.72 | 2.26 |
| 9 | 50 | 2 | 9.33 | 16 | 3.89 | 70.8 | 29.22 | 2.42 |
| 10 | 50 | 10 | 19.2 | 12 | 2.29 | 66.5 | 33.49 | 1.99 |
| 11 | 50 | 10 | 15 | 20.5 | 4.92 | 59.5 | 40.42 | 1.47 |
| 12 | 100 | 2 | 6.83 | 17.5 | 5.11 | 70.6 | 29.44 | 2.40 |
| 13 | 100 | 2 | 13.3 | 19.4 | 5 | 62.2 | 37.7 | 1.65 |
| 14 | 100 | 10 | 11.3 | 18.6 | 4.63 | 65.5 | 34.53 | 1.90 |
| 15 | 100 | 10 | 11.7 | 18.9 | 3.83 | 65.5 | 34.43 | 1.90 |
| 16 | 100 | 10 | 5.19 | 15.8 | 4.42 | 74.6 | 25.41 | 2.94 |

FIG. 4

METHOD AND APPARATUS FOR SELECTIVE REMOVAL OF CELLS FROM A CELL SUSPENSION BY MECHANICAL LYSIS

PRIORITY APPLICATION

This application claims priority to U.S. Provisional Application No. 62/416,609 that was filed on Nov. 2, 2016. The entire content of the application referenced above is hereby incorporated by reference herein.

BACKGROUND

When cells are isolated from tissues for research or diagnostic purposes, the resulting cell suspensions may contain dead and/or dying cells as a result of trauma, insults from disaggregation of tissues and/or pre-existing dead, dying, or fragile cells as in the case of diseased tissue. Dead and dying cells may not be desirable for analytic or experimental procedures aimed at understanding the biology or disease implications of the viable cells within the cell suspension. In scenarios where a patient with a disease is responding less than favorably to current therapy, dead, dying, or fragile cells may indicate cells that are responding to current therapy, and hence, may not be desirable for determining therapeutic strategies aimed at unresponsive cells. Methods exist currently for assessing and separating dead and dying cells from cell suspensions, principally flow cytometry and cell sorting. These methods require the use of exogenous labels (dyes and stains) and evaluate cells one at a time which can take hours to accumulate the desired numbers of viable cells, resulting in undesirable changes in the cells in suspension.

Therapeutic apheresis is used to remove unwanted cellular components from blood. Examples include the removal of sickled red blood cells (RBCs) during sickle cell crisis, or the removal of excess leukocytes in patients with leukemia (erythracytapharesis and leukocytapheresis, respectively). However, current apheresis devices require many complex steps, multiple hours of therapy at a hospital (during which the patient—often a child—has needle access in both arms for blood withdrawal and return), and causes all cells of the given type (i.e. all RBCs) to be sacrificed, thus requiring donor blood and associated costs, risks, and complications.

For these and other reasons there is a need for the subject matter of the present disclosure.

SUMMARY

In some embodiments, a method for selectively lysing cells from a cell suspension includes subjecting the cell suspension to at least one pulse of mechanical stress to lyse one or more targeted cells.

In some embodiments, a method includes disassociating a population of cells from a tissue sample, the population of cells including a population of one or more viable cells and a population of one or more dead or dying cells, exposing the population of cells to at least one pulse of fluid shear stress to substantially lyse the population of one or more dead or dying cells, leaving the population of one or more viable cells substantially intact, and enriching the population of one or more viable cells in the population of cells.

In some embodiments, a fluid handling system for applying a plurality of pulses of fluid shear stress to a fluid sample, the system includes a first sample chamber, a second sample chamber, a plurality of conduits mounted between and in fluid communication with the first sample chamber and the second sample chamber, the plurality of conduits having substantially similar dimensions and inner diameters of less than about 1000 micrometers, and a force delivery system mounted to the first sample chamber and configured to apply a selected force sufficient to push the fluid sample from the first sample chamber through each of the conduits at a substantially constant flow rate to the second sample chamber.

BRIEF DESCRIPTION OF DRAWINGS

FIG. 4 shows a table of Example 4 data for isolation of target cells from melanoma tissue in accordance with some embodiments of the present disclosure.

DETAILED DESCRIPTION

Figure 1A:
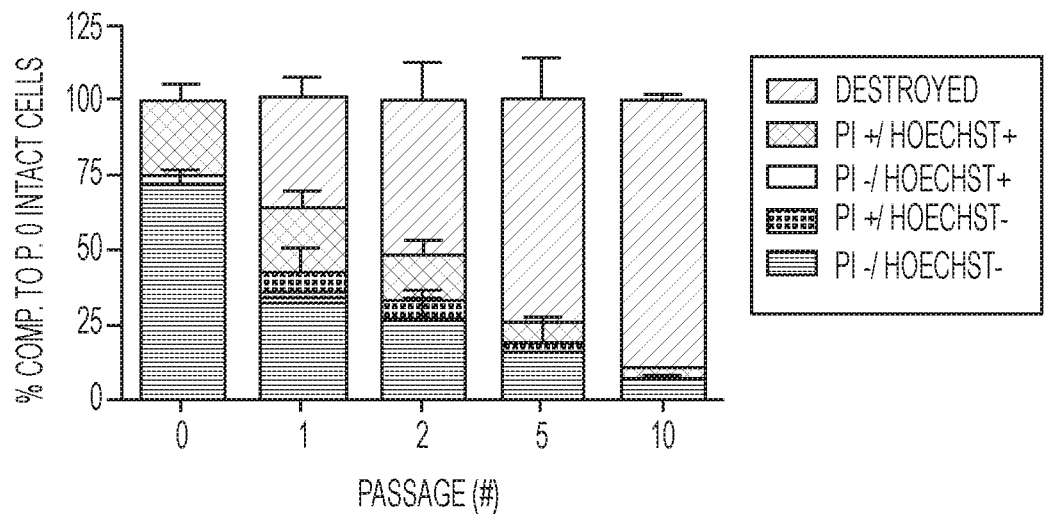
FIG. 1A shows Example 1 data for a fluid suspension of benign prostate cells exposed to pulses of fluid shear stress in a conduit in a range from 750-6500 dyn/cm$^2$ for ~1 msec in accordance with some embodiments of the present disclosure.

In some embodiments, the subject matter of present disclosure describes a selective process to rapidly remove certain cells from a fluid suspension of cells using mechanical lysis. Application of mechanical stress selectively lyses cells on the basis of biomechanical differences among different classes, types, or viability status of cells. The subject matter of the disclosure is useful for the fields of basic scientific research, medical diagnostics, and therapeutics. In one embodiment, the subject matter of the disclosure will improve a variety of subsequent laboratory procedures by selective removal of dead and dying cells where a purified preparation of viable cells is desirable. In another embodiment, comparing the ratio of cells before and after exposure to mechanical stress tuned to remove dead and dying cells will define a viable cell fraction for that sample. In a third embodiment, dying or mechanically fragile cells can be removed from a heterogeneous tissue (e.g. blood) for therapeutic purposes.

The presence of dead and dying cells in cell suspensions is a hindrance to a number of common and emerging laboratory research, diagnostic, and therapeutic techniques such as flow cytometry and fluorescence-activated cell sorting, genetic analysis, cytology, gene transfer, cell transplantation, and blood storage. Dead or dying cells obscure results focused on the biology of viable cells and may require additional efforts (time/costs) to account for the presence of dead cells, such as fluorescence-activated cell sorting or genetic analysis of single cells.

There is commercial value in a device that rapidly destroys and thus removes dead and dying cells from cell suspensions. Current methods for identification and removal of dead and dying cells rely on fluorescence-activated cell sorting using labels (certain stains and dyes) and are evaluated a single cell at a time, often taking hours. In some embodiments, the subject matter of present disclosure provides a method for removing dead and dying cells without using labels which can be rapidly applied to bulk cells preparations. In another embodiment, by increasing the level of mechanical stress, dead, dying, and viable cells can be removed from a cell suspension to isolate malignant cells as described in U.S. Pat. No. 9,063,118 B2. Other embodiments can potentially remove different classes and types of cells by selective tuning of the mechanical stresses.

The subject matter of the present disclosure is a process by which a fluid cell suspension is exposed to mechanical stresses designed to lyse particular classes, types of cells, or states of cells (i.e., dead vs. viable, malignant vs. benign, etc.) by virtue of differences in the cells' resistance to mechanical forces. The use and modulation of biomechanical forces applied in the context of selectively lysing certain classes, types, or states of cells from bulk fluid suspensions is a novel aspect of this disclosure. Mechanical stimuli (such as force, stress, pressure, strain) above can be applied and modulated via a number of means including passage of the fluid suspension through channels or restrictions of the appropriate specifications, at appropriate rates, to deliver fluidic forces or stress (under laminar or turbulent flow), via passage of the fluid suspension through suitably designed pores or channels to apply suitable fluid stress for suitable duration, via passage of the fluid suspension through suitably designed pores or channels to mechanically constrict or strain cells, via time-dependent, controlled changes in pressure of the fluid suspension, via exposure of the fluid suspension to pulses of ultrasound, via controlled impact of the fluid suspension against a solid surface, and the like. After processing, the remaining intact cells are viable. These target cells can be collected by standard means including but not limited to, simple density gradient centrifugation, size-based filtration, cell sorters, or microfluidics.

In one embodiment, the sample is subjected to brief (<1-100 millisecond (msec)) repeated (1-1000) pulses of mechanical stress (1-20,000 dyn/cm$^2$) that selectively lyse (causes disintegration of the plasma membrane and release of cytoplasmic contents) the targeted subset of cells (dead and dying), whereas the non-targeted (viable) cells are largely resistant to these treatments. In another embodiment, removal of dead and dying cells is achieved with another method of mechanical stress including those listed above. In another embodiment, by increasing the level of mechanical stress, dead, dying and healthy cells can be removed from a cell suspension to isolate malignant cells as described in U.S. Pat. No. 9,063,118 B2. In another embodiment, by modulating the time that the sample is subjected to the mechanical stimuli, the targeted subset of cells is lysed and the remaining cells remain intact. Other embodiments can potentially remove different classes, types, or states of cells by selective tuning of the mechanical stresses (for example changing magnitude, duration, rate of change) from any appropriate source including those listed above. In one embodiment, using any of the selective lysing embodiments described above, a viable cell fraction can be calculated for the sample, by comparing the ratio of cells before and after exposure to mechanical stress.

In some embodiments, the samples are cells in an aqueous suspension that is forced through a hollow needle, such as hypodermic needles or needle-like tubes. The pressure to push the fluid through the needles is generated by mechanical force on a plunger (like a hypodermic syringe) or by gas pressure. This method provides the ability to regulate the forces to the conditions described.

The subject matter of present disclosure has utility in a variety of applications. For example, the subject matter of the present disclosure can be used in life science research, such as for single cell genetic analysis, preparation of body fluids, tumor and tissue specimens for genetic analysis, preparation of tissue specimens for flow cytometry and cell sorting (or as alternatives to the same), preparation of tissue specimens for cell transplantation, or preparation of tissue specimens for gene transfer. In some embodiments, the subject matter of the present disclosure can be used for diagnostics, such as the preparation of body fluids and tissue biopsies for diagnostic procedures such as genetic, histologic, pathologic, cytologic, and flow cytometry analysis. In some embodiments, the subject matter of the present disclosure can be used for therapeutics, such as the removal of dying RBCs from whole blood or packed RBCs to improve storage life; therapeutic apheresis to remove dying or fragile cells from circulation. In the above cases, knowledge of the viable cell fraction of the sample can be a useful metric for characterizing sample quality.

The subject matter of the present disclosure will now be illustrated by the following non-limiting examples.

Example 1

Figure 1B:
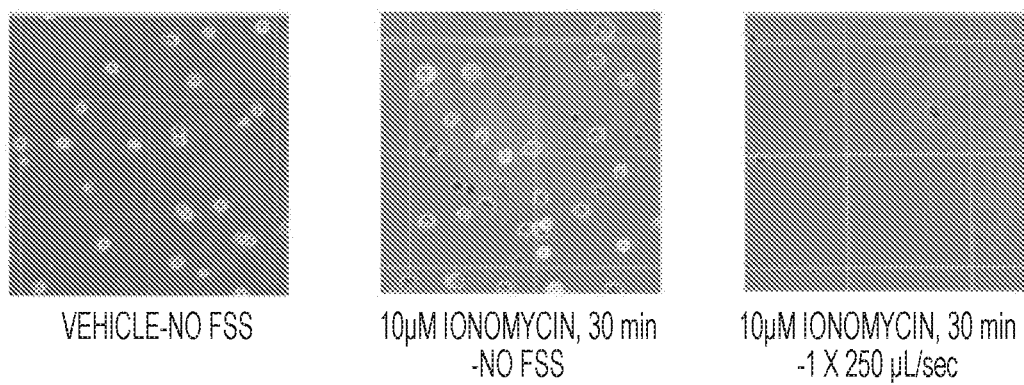
FIG. 1B shows Example 1 data for a fluid suspension of benign prostate cells treated with ionomycin and cells and exposed to one pulse of 750-6500 dyn/cm$^2$ for ~1 msec which causes lysis of all of the cells, as only cell debris is apparent microscopically in accordance with some embodiments of the present disclosure.
Figure 1B:
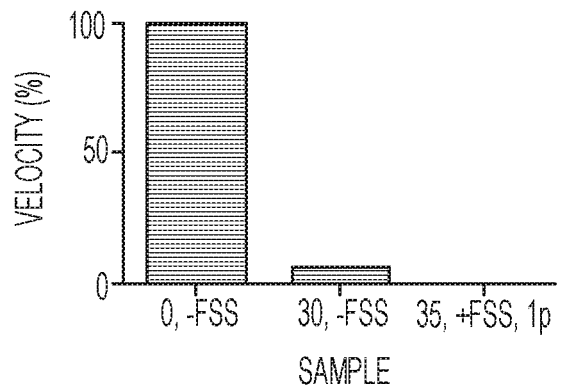

A fluid suspension of benign prostate cells was exposed to pulses of fluid shear stress in a conduit in a range from 750-6500 dyn/cm2 for ~1 msec. In FIG. 1A, the light bar indicates dead cells detectable by the presence of membrane impermeant dyes (PI; Hoescht). The black and dotted bars are viable cells. That fraction progressively lyses (destroyed) with repeated pulses. In a different mode, lower-level mechanical force is applied that does not damage living cells, but lyses dead/dying cells to measure the viable cell fraction in the sample. In FIG. 1B, prostate cancer cells were treated with ionomycin, which rapidly kills these cells after 30 minute as measured by uptake of trypan blue dye. Exposure of one pulse of 750-6500 dyn/cm$^2$ for ~1 msec causes lysis of all of the cells, as only cell debris is apparent microscopically.

Example 2

Figure 2A:
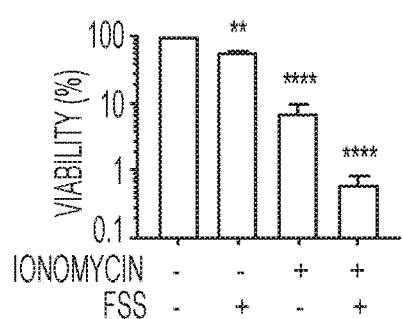
FIG. 2A shows Example 2 data where PC-3 cells were treated with 10 μM ionomycin for 60 minutes and where treated and untreated cells were exposed to one pulse of fluid shear stress at 250 μL/sec in accordance with some embodiments of the present disclosure.
Figure 2B:
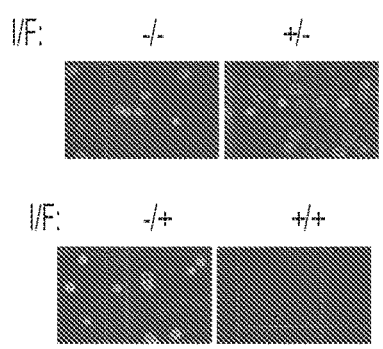
FIG. 2B shows Example 2 data for untreated and treated cells before and after fluid shear stress in accordance with some embodiments of the present disclosure.
Figure 2C:
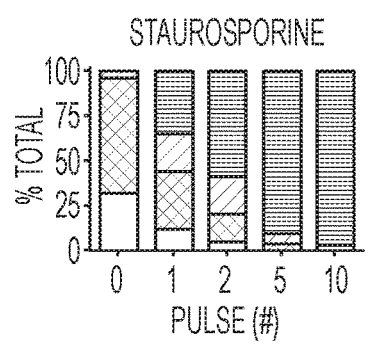
FIG. 2C shows Example 2 data for cell fractions treated with 4 μM staurosporine for four hours and exposed to fluid shear stress in accordance with some embodiments of the present disclosure.
Figure 2D:
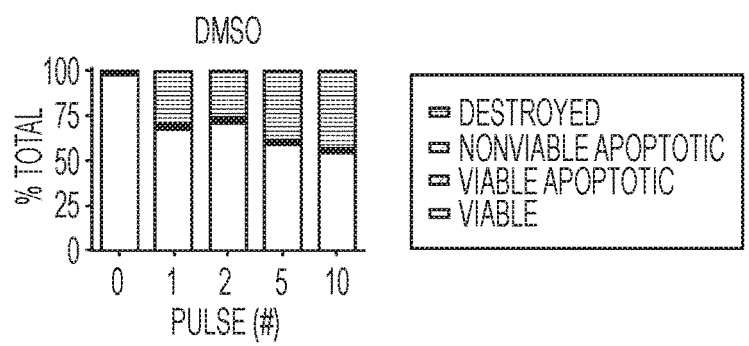
FIG. 2D shows Example 2 data for DMSO control cell fractions in accordance with some embodiments of the present disclosure.

PC-3 cells were treated with 10 μM ionomycin for 1 hour (FIGS. 2A, 2B) or 4 μM staurosporine for 4 hours (FIGS. 2C, 2D). Treated and control cells were released with 0.25% trypsin, counted, centrifuged at 300 g for 5 minutes, and resuspended to 500 k cells/mL in DMEM. Duplicate samples were taken before and after exposure to either 1, 2, 5, or 10 pulses of fluid shear stress at a flow rate of 250 μL/sec. Ionomycin and respective controls were measured with bioluminescent imaging in an AMI-1000 for 300 seconds. Images were taken on a hemacytometer to assess intact treated cells. Staurosporine and control samples were centrifuged at 300 g for 5 minutes and resuspended in Cell Staining Buffer (BioLegend, 420201) to wash. Cells were washed again then resuspended in 1× Annexin V Binding Buffer (BioLegend, 422201) at 1×10$^6$ cells/mL. 100 μL of the sample was transferred to a new tube, 5 APC-conjugated Annexin V (BioLegend, 640920) was added, and then incubated for 15 minutes in the dark. 400 μL Annexin V Binding Buffer was added containing 10 μL/mL Hoechst 33258 and fluorescent beads at a ratio of 1:20. Intact cell counts were standardized to counting beads. Subsequent loss of intact events after fluid shear stress indicates lysis of dead cells.

Samples were analyzed on a BD LSR flow cytometer. Annexin-V+/Hoechst-33258− cells were considered viable and apoptotic, Annexin-V−/Hoechst-33258− cells were viable, and cells Hoechst-33258+ were dead, intact cells.

Example 3

Figure 3A:
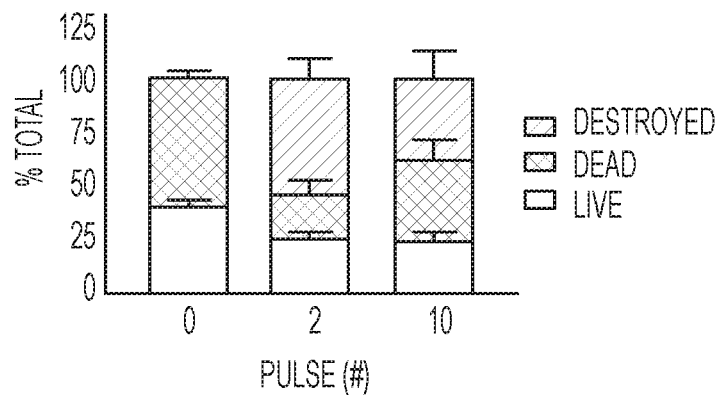
FIG. 3A shows Example 3 data for PC-3 cells exposed to fluid shear stress at 20 μL/sec for 2 or 10 pulses and dead cells generated with 10 μM ionomycin for 1 hour (n=2) in accordance with some embodiments of the present disclosure.
Figure 3B:
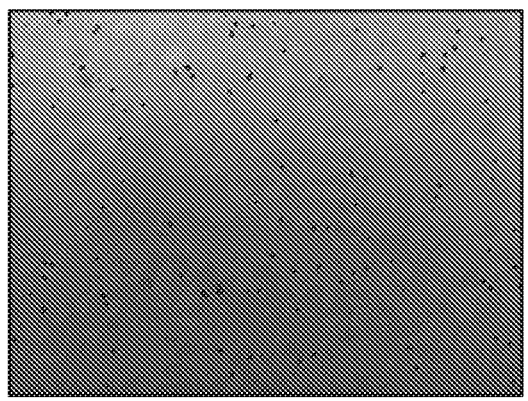
FIG. 3B shows an Example 3 representative image of unexposed, mixed cells in accordance with some embodiments of the present disclosure.
Figure 3C:
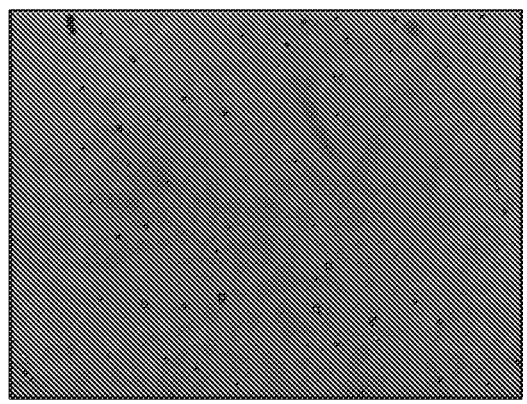
FIG. 3C shows Example 3 data for mixed cells exposed to 2 pulses at 20 μL/sec in accordance with some embodiments' of the present disclosure.

PC-3 cells were treated with 10 μM ionomycin for 1 hour (FIG. 3A). Untreated PC-3 cells were released with 0.25% Trypsin. Treated and untreated cells were counted, centrifuged at 300 g for 5 minutes, and resuspended to 500 k cells/mL. Untreated cells and treated cells were mixed at a ratio of 1:2 (FIG. 3B). Duplicate samples were taken before exposure to fluid shear stress and after 2 and 10 pulses at a flow rate of 20 μL/sec (FIG. 3C). The substantially square/rectangular conduit employed in Example 3 is similar to the conduit employed in the device shown in FIG. 11A of WO 2016/070007. Samples were mixed 1:1 with Trypan Blue and counted with a LUNA-II. Destroyed cells were inferred from the difference between total intact cell events at pulses 2 and 10 compared to the unexposed control.

Example 4

The melanoma tumor was transferred to a 10 cm petri dish containing 10 mL collagenase IV solution (9 mL HBSS−/−+1 mL collagenase IV+50 μL CaCl$_2$). The sample was minced as small as possible. The minced tissue was incubated 1-2 hours at 37° C. 10 mL HBSS−/− was added to the dish. Tissues were transferred to a 50 mL tube, centrifuged at 500 g for 5 minutes and the supernatant removed. Sample was resuspended in 10 mL 1×TEG buffer or 10 mL 0.05% Trypsin solution and incubated in 37° C. water bath for 10 minutes. 10 mL complete medium was added to stop the reaction. Pass sample through 16 or 18 gauge needles 30 times. The suspension was filtered with a 70 μM cell strainer, centrifuged at 500 g for 5 minutes, and the supernatant was removed. The sample was resuspended in 10 mL DMEM medium. 100 μL of the cell suspension was mixed with 100 μL trypan blue and counted in a hemacytometer. Volume was adjusted to 1×10$^6$ cells/mL. 5 mL samples were exposed to fluid shear stress at different flow rates and pulse numbers. 500 μL samples were taken at 0, 2, and 10 pulses. The substantially square/rectangular conduit employed in Example 4 is similar to the conduit employed in the device shown in FIG. 11A of WO 2016/070007. Samples were centrifuged at 300 g for 3 minutes and resuspended in 100 μL 1× Assay Buffer (Santa Cruz Biotechnology, sc-4252AK). 5 μL FITC-conjugated Annexin V (Santa Cruz Biotechnology, sc-4252AK) was added, and incubated for in the dark for 30 minutes. 400 μL 1× Assay Buffer was added containing 10 μL/mL Hoechst 33258 and fluorescent beads at a ratio of 1:20. Samples were analyzed on a BD LSR flow cytometer. Cells in Q1, FITC-A−/Hoechst-33258-A+, are dead, Q2 FITC-A+/Hoechst-33258-A− cells are dead apoptotic cells, Q3 FITC-A+/Hoechst-33258-A− cells are viable apoptotic cells, and Q4 FITC-A−/Hoechst-3328-A− cells are non-apoptotic, viable cells. The ratio of Q4:(Q1+Q2+Q3) was calculated to determine reduction of the dead/dying population and enrichment of viable cells (FIG. 4).

Example 5

Figure 5A:
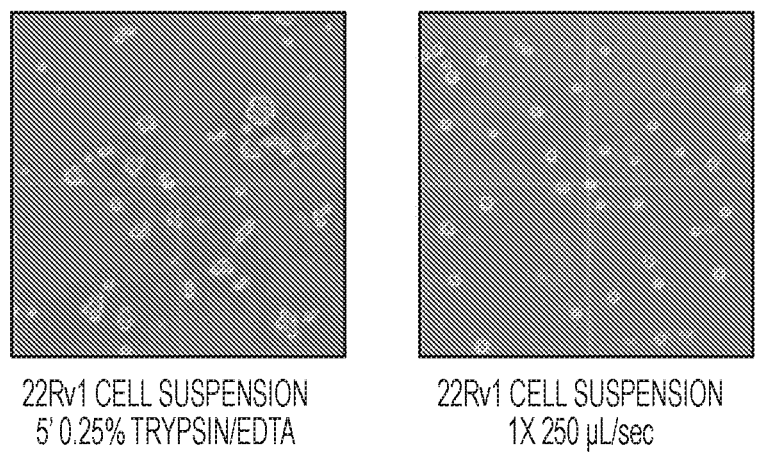
FIG. 5A shows Example 5 data for clusters in suspension after standard trypsinization in accordance with some embodiments of the present disclosure.
Figure 5B:
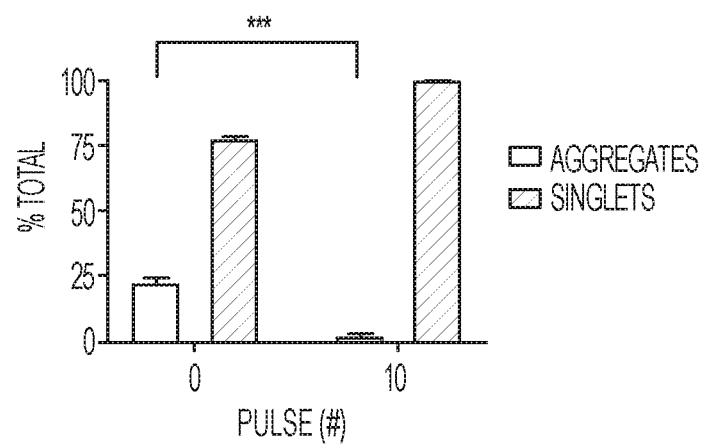
FIG. 5B shows Example 5 data for disruption of cell aggregates by exposure to fluid shear stress in accordance with some embodiments of the present disclosure.

FIG. 5A shows that 22Rv1 typically remain as clusters in suspension after standard trypsinization, but after a single pulse of fluid shear stress the suspension is predominantly single cells. FIG. 5B show PC-3 cell suspension is exposed to fluid shear stress in complete medium at 250 uL/sec for 10 passages. Single cells and aggregates (>1 cell together) are quantified with a hemacytometer (***, p<0.001. Repeated measures ANOVA, Bonferroni's multiple comparison test, n=4).

In certain embodiments in the disclosure a method is described which includes a step of disassociating a population of cells from a tissue sample. The tissue sample can be any tissue from an organism, for example from a plant or an animal. Tissue samples include for example, brain tissue, tumor tissue, lung tissue, skin tissue, heart tissue, bladder tissue, organ tissue, endosperm tissue, leaf tissue, and any tissue known to one of ordinary skill in the art. One of ordinary skill in the art will appreciate that such tissue samples are in many cases not homogeneous and include cells from a variety of origins, for example endothelial cells and immune cells can be found in a single tissue sample. Disassociation as used herein refers to breaking up the tissue sample into smaller portions, for example into clusters of cells and individual cells. The disassociation step can include for example mechanical manipulation of the tissue sample, chemical treatment of the tissue sample, enzymatic treatment of the tissue sample, or combinations thereof. The resulting clusters of cells and individual cells are a population of cells that include viable cells and dead and dying cells. The population of viable cells can be referred to as a subpopulation of the disassociated cells. Similarly, the population of dead and dying cells can be referred to as a subpopulation of the disassociated cells.

Using the teachings provided herein one of ordinary skill in the art can establish the parameters of force and duration of fluid shear stress (FSS) to which the population of cells is exposed to appropriately separate the population of cells into a population of lysed dead and dying cells and a population of viable cells. For example, an average force duration from about 1 milliseconds to about 100 milliseconds, or from about 3 milliseconds to about 20 milliseconds, or from about 10 milliseconds to about 20 milliseconds, can be used to substantially lyse the dead and dying cell population while substantially maintaining the viable cell population. Substantially as used herein refers to reducing the population of dead and dying cells by at least 40, 50, 60, 70, 80, or 90% as determined by comparing the population prior to the FSS exposure to the population after FSS. Similarly, substantially as used herein refers to maintaining the population of viable cells from the population of cells such that at least 50, 60, 70, 80, or 90% of the viable cells in the population of cells is present after exposure to the FSS.

The FSS as described herein has a force and a duration component that one of ordinary skill in the art will appreciate is impacted by the conduit physical characteristic, such as length, diameter and shape. The population of cells can be exposed to a FSS having a force along a conduit wall of from about 500 dyn/cm2 to about 2500 dyn/cm2 to substantially lyse the population of one and more dead or dying cells, leaving the population of one or more viable cells substantially intact. Depending upon the nature of the tissue sample and the population of cells, one of ordinary skill in the art will appreciate that other forces can be used, for example from about 600 dyn/cm2 to about 1500 dyn/cm2, from about 750 dyn/cm2 to about 1500 dyn/cm2, or from about 850 dyn/cm2 to about 1500 dyn/cm2 can be used.

After exposure to the FSS the population of viable cells can be collected and in some embodiments the population of lysed cells can also be collected. The collection can be accomplished using any method that separates the viable cells substantially from the lysed dead and dying cells, for example, centrifugation, filtration, sedimentation, cells sorters, microfluidics and combinations thereof.

In some embodiments the method provides for isolating individual cells which is useful, among other things, for studying the cell and its biochemical status. The method is advantageous because the FSS allows the individual cell to be isolated quickly from the tissue and therefore, remain biochemically in a state more similar to the biochemical state is was in when it was in the intact tissue. In some instances, the method can produce an individual viable cell from the population of cells produced by the disassociation in less than 4 hours, less than 3.5 hours, less than 3 hours, less than 2.5 hours, less than 2 hours, 1.5 hours, or less than an hour. The relatively quick method increases the likelihood that the biochemical status of the isolated individual cell will be similar to that of the cell when it was in the tissue sample.

The biochemical status of the individual cells can be characterized by detecting molecules such as nucleic acid sequences, amino acid sequences, inorganic species, and carbohydrates that are present in the cell. In some instances the population of transcribed RNA species in a cell can be characterized to determine the metabolic pathways that are active within the cell. In some instances the RNA population can be characterized and the proteins expressed can be characterized to determine biochemical pathway control mechanisms.

In some embodiments the method can be used to characterize the individual cells. For example, using methods known in the art, the individual cells can be contacted with specific binding agents to identify the cell as a stem cell, immune cell, pre-cancerous cell, or viral infected cell.

Figure 6:
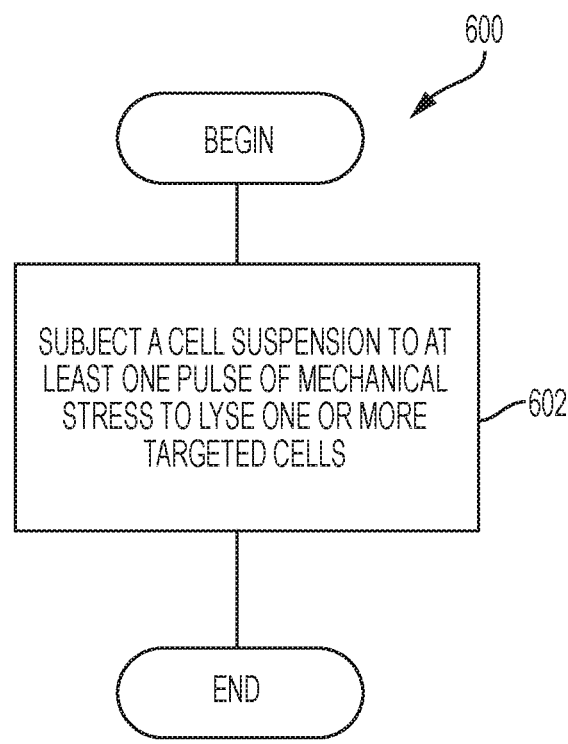
FIG. 6 shows a flow diagram of a method for lysing cells in accordance with some embodiments of the present disclosure.

FIG. 6 shows a flow diagram of a method 600 for lysing cells in accordance with some embodiments of the present disclosure. The method 600 for selectively lysing cells from a cell suspension includes subjecting the cell suspension to at least one pulse of mechanical stress to lyse one or more targeted cells (block 602). In some embodiments, subjecting the cell suspension to the at least one pulse of mechanical stress to lyse the one or more targeted cells includes for the at least one pulse of mechanical stress having a pulse duration, subjecting the cell suspension to the pulse duration of between about 1 millisecond and about 100 milliseconds. In some embodiments subjecting the cell suspension to the pulse duration of between about 1 millisecond and about 100 milliseconds includes for the at least one pulse of mechanical stress having a force, subjecting the cell suspension to the force of between about 1 dyn/cm2 and about 20,000 dyn/cm2.

The disclosure is not limited to the method 600. Exemplary additional methods include the variations of method 600. In some embodiments, the methods substantially avoid lysing non-targeted cells in the cell suspension. In some embodiments, the method does not lyse non-targeted cells in the cell suspension. In some embodiments, the targeted cells are dead or dying cells. In some embodiments, the non-targeted cells are viable. In some embodiments, the targeted cells are un-labeled. In some embodiments, subjecting the cell suspension to the at least one pulse of mechanical stress to lyse the one or more targeted cells includes for the at least one pulse of mechanical stress having a pulse duration, subjecting the cell suspension to the pulse duration of between about 1 millisecond and about 10 milliseconds. In some embodiments, subjecting the cell suspension to the pulse duration of between about 1 millisecond and about 100 milliseconds includes for the at least one pulse of mechanical stress having a force, subjecting the cell suspension to the force of between about 650 dyn/cm$^2$ and about 6,500 dyn/cm$^2$. In some embodiments, the non-targeted cells are malignant cells. In some embodiments, subjecting the cell suspension to the at least one pulse of mechanical stress to lyse the one or more targeted cells includes forcing the cell suspension through a tube. Exemplary tubes include syringe needs and needle-like tubes. In some embodiments, the method 600 further includes removing the targeted cells from the cell suspension. In some embodiments, removing the targeted cells from the cell suspension includes removing the targeted cells by density gradient centrifugation, size-based filtration, cell sorters, or microfluidics.

Figure 7:
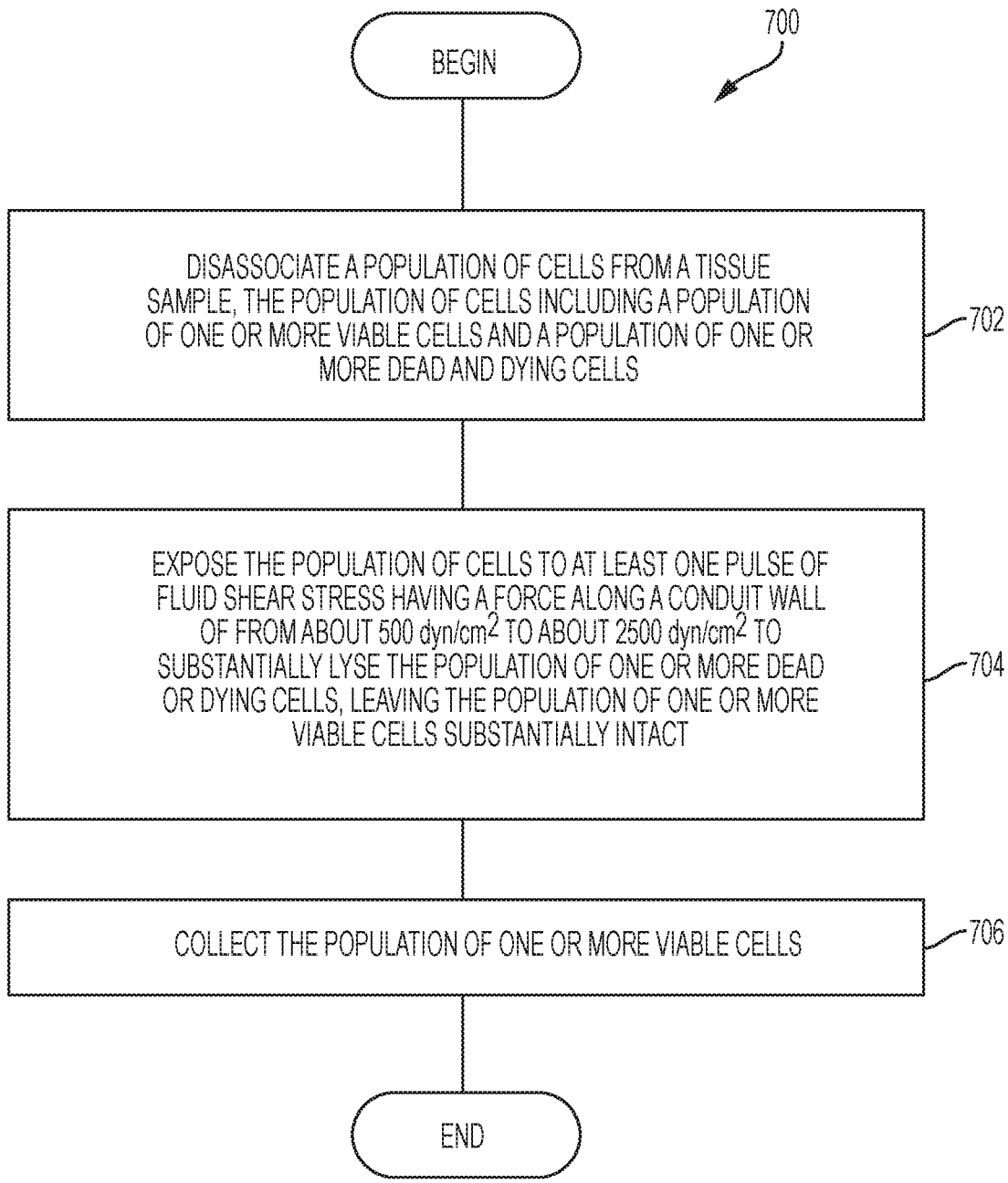
FIG. 7 shows a flow diagram of a method for lysing disassociated cells for a tissue sample in accordance with some embodiments of the preset disclosure.

FIG. 7 shows a flow diagram of a method 700 for lysing cells disassociated for a tissue sample in accordance with some embodiments of the preset disclosure. The method 700 includes disassociating a population of cells from a tissue sample, the population of cells including a population of one or more viable cells and a population of one or more dead or dying cells (block 702), exposing the population of cells to at least one pulse of fluid shear stress having a force along a conduit wall of from about 500 dyn/cm$^2$ to about 2500 dyn/cm$^2$ to substantially lyse the population of one or more dead or dying cells, leaving the population of one or more viable cells substantially intact (704), and collecting the population of one or more viable cells (706).

In some embodiments, enriching the population of the one or more viable cells in the population of cells includes applying centrifugation to the population of cells. In some embodiments, enriching the population of the one or more viable cells in the population of cells includes applying filtration to the population of cells. And in some embodiments, enriching the population of the one or more viable cells in the population of cells includes applying sedimentation to the population of cells.

In some embodiments, at least about 80% of the viable cells survive the fluid shear stress. In some embodiments, the methods further include isolating a single viable cell, wherein the time to isolate the single viable cell from the disassociated population of cells is less than about 2 hours. In some embodiments, the population of cells from a tissue sample is nonhomogeneous. In some embodiments, the single cell includes transcribed RNA and wherein the transcribed RNA is characterized.

In some embodiments, the methods further include contacting the single cell with specific binding agents and wherein the binding of an agent identifies the cell as a stem cell, immune cell, pre-cancerous cell, or oviral infected cell. In some embodiments, the dissociated cell population is exposed to at least two pulses of fluid shear stress and wherein the at least two pulses of fluid shear stress are substantially the same. In some embodiments, the methods further include extracting the population of one or more dead or dying cells. And the methods further include analyzing the population of one or more dead or dying cells.

Figure 8:
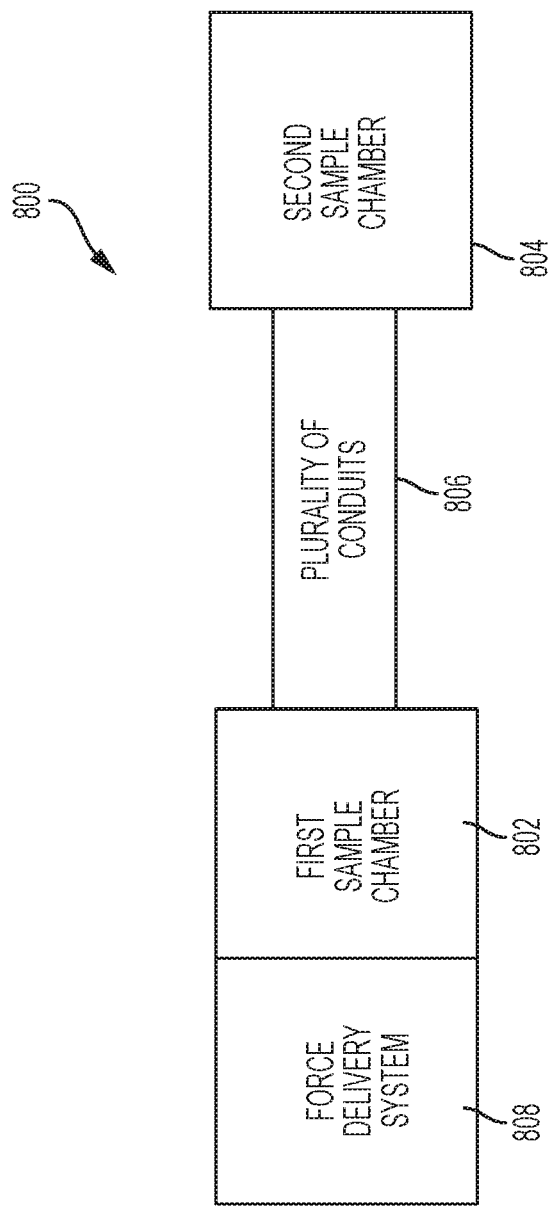
FIG. 8 shows a block diagram of a fluid handling system in accordance with some embodiments of the present disclosure.

FIG. 8 shows a block diagram of a fluid handling system 800 in accordance with some embodiments of the present disclosure. The fluid handling system 800 includes a first sample chamber 802, a second sample chamber 804, a plurality of conduits 806 mounted between and in fluid communication with the first sample chamber 802 and the second sample chamber 804, and a force delivery system 808. In operation, the fluid handling system 800 applies a plurality of pulses of fluid shear stress to a fluid sample in the first sample chamber 802. The force delivery system 808 is mounted to the first sample chamber 802 and configured to apply a selected force sufficient to push the fluid sample from the first sample chamber 802 through each of the plurality of conduits at a substantially constant flow rate to the second sample chamber 804. In some embodiments, each of the plurality of conduits has substantially similar dimensions and inner diameters of less than about 1000 micrometers.

Figure 9:
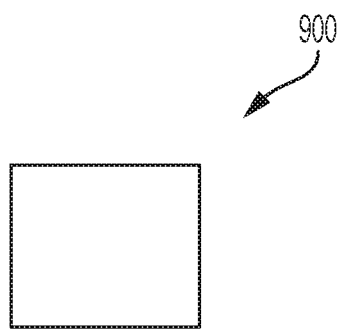
FIG. 9 shows an illustration of a cross-sectional view of a substantially rectangular conduit in accordance with some embodiments of the present disclosure.

FIG. 9 shows an illustration of a cross-sectional view 900 of one of the plurality of conduits 806 (shown in FIG. 8) in accordance with some embodiments of the present disclosure. The cross-section of each of the one of the plurality of conduits 806 is not limited to a particular shape. In some embodiments, the cross-sectional shape is substantially rectangular.

Figure 10:
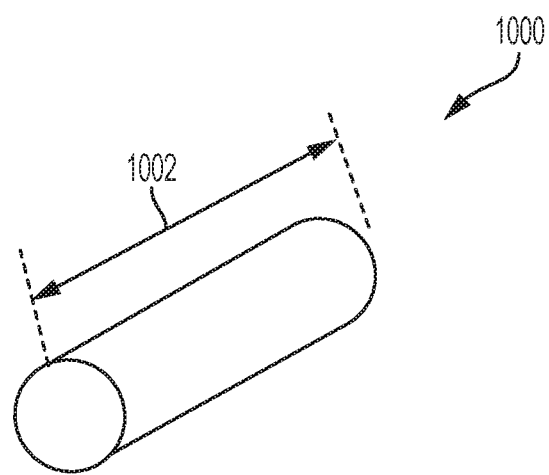
FIG. 10 shows an illustration of one or more channels in accordance with some embodiments of the present disclosure.

FIG. 10 shows an illustration of one or more channels 1000 in accordance with some embodiments of the present disclosure. Each of the one or more channels 1000 has a length 1002. The length 1002 is not limited to a particular value.

Although the foregoing specification and examples fully disclose and enable the subject matter of present disclosure, they are not intended to limit the scope of the claims appended hereto.

All publications, patents and patent applications are incorporated herein by reference. While in the foregoing specification the subject matter of the disclosure has been described in relation to certain embodiments, and many details have been set forth for purposes of illustration, it will be apparent to those skilled in the art that the disclosure is susceptible to additional embodiments and that certain of the details described herein may be varied considerably without departing from the basic principles included in the disclosure.

The use of the terms "a" and "an" and "the" and similar referents in the context of the disclosure are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the disclosure and does not pose a limitation on the scope of the disclosure unless otherwise claimed. No language in the specification should be construed as indicating any non-claimed element as essential to the practice of the subject matter of the disclosure.

Embodiments are described herein, including the best mode known to the inventors for carrying out the subject matter of the disclosure. Variations of those embodiments may become apparent to those of ordinary skill in the art upon reading the foregoing description. The inventors expect skilled artisans to employ such variations as appropriate, and the inventors intend for the subject matter of the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method comprising:
    disassociating a population of cells from a tissue sample, the population of cells including a population of one or more viable cells and a population of one or more dead and dying cells;
    exposing the population of cells to at least one pulse of fluid shear stress having a force along a conduit wall of from about 500 dyn/cm2 to about 2500 dyn/cm2 to substantially lyse the population of one or more dead or dying cells, leaving the population of one or more viable cells substantially intact; and
    collecting the population of one or more viable cells.

2. The method of claim 1, further comprising isolating at least one individual cell from the population of one or more viable cells.

3. The method according to claim 2, wherein the isolation of at least one individual cell from the population of cells is accomplished in less than 4 hours.

4. The method of claim 2, further comprising isolating a population of nucleic acid sequences from the at least one individual cell, wherein the population of nucleic acid sequences has not substantially changed from prior to disassociation.

5. The method of claim 2, further comprising isolating a population of amino acid sequences from the at least one individual cell, wherein the population of amino acid sequences has not substantially changed from prior to disassociation.

6. The method of claim 2, wherein the isolation of at least one individual cell from the population of cells is accomplished in less than 3.5 hours.

7. The method of claim 2, wherein the at least one individual cell comprises transcribed RNA and wherein the transcribed RNA is characterized.

8. The method of claim 1, wherein exposing the population of cells to the at least one pulse of fluid shear stress comprises at least one pulse having a duration of between about 1 millisecond and about 10 milliseconds.

9. The method of claim 1, wherein the exposing the population of cells to the at least one pulse of fluid shear stress comprises exposing the population of cells to the at least one pulse of fluid shear stress having a force of between about 500 dyn/cm$^2$ and about 2,500 dyn/cm$^2$ with the force being measured along a conduit wall wherein the at least one pulse of fluid shear stress has a force of between about 850 dyn/cm$^2$ and about 1500 dyn/cm$^2$.

10. The method of claim 1, wherein collecting the population of one or more viable cells from the population of cells comprises substantially removing the lysed dead and dying cells by density gradient centrifugation, centrifugation, size-based filtration, cell sorters, or microfluidics.

11. The method of claim 1, wherein the exposing the population of cells to the at least one pulse of fluid shear stress comprises exposing the population of cells to the at least one pulse of fluid shear stress having a force of between about 600 dyn/cm$^2$ and about 1,500 dyn/cm$^2$ with the force being measured along a conduit wall.

12. The method of claim 1, wherein at least about 90% of the viable cells survive the fluid shear stress.

13. The method of claim 1, wherein the population of cells from a tissue sample is nonhomogeneous.

14. The method of claim 1, wherein a population of cells is exposed to at least two pulses of fluid shear stress and wherein the at least two pulses of fluid shear stress are substantially the same.

15. The method of claim 1, further comprising collecting the lysed dead and dying cells.

16. The method of claim 15, further comprising characterizing the nucleic acid sequences or amino acid sequences in the collected lysed dead and dying cells.

\* \* \* \* \*